(12) United States Patent
Cohen et al.

(10) Patent No.: US 10,176,630 B2
(45) Date of Patent: Jan. 8, 2019

(54) UPDATING AN ELECTROANATOMICAL MAP

(71) Applicant: BIOSENSE WEBSTER (ISRAEL) LTD., Yokneam (IL)

(72) Inventors: Assaf Cohen, Kiryat Bialik (IL); Ido Ilan, Yoqneam (IL); Fady Massarwi, Baka Al Gharbiyya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 24 days.

(21) Appl. No.: 15/370,327

(22) Filed: Dec. 6, 2016

(65) Prior Publication Data

US 2018/0158238 A1 Jun. 7, 2018

(51) Int. Cl.
*G06T 15/00* (2011.01)
*G06T 17/20* (2006.01)
(Continued)

(52) U.S. Cl.
CPC .......... *G06T 17/20* (2013.01); *A61B 5/04012* (2013.01); *A61B 5/0422* (2013.01);
(Continued)

(58) Field of Classification Search
CPC ... A61B 5/0422; A61B 18/12; A61B 18/1206; A61B 18/1492; A61B 2018/00351;
(Continued)

(56) References Cited

U.S. PATENT DOCUMENTS 5,487,391 A * 1/1996 Panescu ............... A61B 5/0538
600/374
8,271,095 B2 * 9/2012 O'Sullivan ........ A61B 18/1492
607/116
(Continued)

FOREIGN PATENT DOCUMENTS

EP 2 712 543 A1 4/2014

OTHER PUBLICATIONS

Peters J, Ecabert O, Meyer C, Schramm H, Kneser R, Groth A, Weese J. Automatic whole heart segmentation in static magnetic resonance image volumes. InInternational Conference on Medical Image Computing and Computer-Assisted Intervention Oct. 29, 2007 (pp. 402-410). Springer, Berlin, Heidelberg.*
(Continued)

*Primary Examiner* — Phu K Nguyen
(74) *Attorney, Agent, or Firm* — Dergosits & Noah LLP; Todd A. Noah

(57) ABSTRACT

Described embodiments include a system for updating a mesh, which includes a plurality of vertices, representing a surface of a heart. The system includes an electrical interface and a processor. The processor is configured to define a plurality of sample points on the mesh, such that a density of the sample points is greater than a density of the vertices, to receive, via the electrical interface, a plurality of signals from a catheter, the signals indicating an electrical property of each of a plurality of locations on the surface, and to update the mesh in accordance with the electrical property, by, for each of the locations, identifying a closest sample (Continued)

point to the location, subsequently, identifying, in a portion of the mesh in which the closest sample point is located, a closest point to the location, and, subsequently, associating the closest point with the electrical property of the location.

20 Claims, 3 Drawing Sheets

(51) Int. Cl.
  *A61B 5/042*  (2006.01)
  *A61B 5/04*  (2006.01)
  *A61B 5/00*  (2006.01)
  *G06T 19/20*  (2011.01)

(52) U.S. Cl.
  CPC ............ *A61B 5/743* (2013.01); *G06T 17/205* (2013.01); *G06T 19/20* (2013.01); *G06T 2207/30048* (2013.01); *G06T 2210/41* (2013.01); *G06T 2210/56* (2013.01); *G06T 2219/2012* (2013.01)

(58) Field of Classification Search
  CPC ..... A61B 5/4836; A61B 5/743; A61B 5/0044; A61B 5/04011; A61B 5/044
  USPC .......................................................... 345/418
  See application file for complete search history.

(56) References Cited

U.S. PATENT DOCUMENTS

| | | | | |
|---|---|---|---|---|
| 8,355,801 | B2 * | 1/2013 | O'Sullivan | ........ A61B 18/1492 607/116 |
| 8,648,855 | B2 | 2/2014 | Pedersen | |
| 9,171,396 | B2 | 10/2015 | Jenkins | |
| 9,241,667 | B2 * | 1/2016 | Narayan | ............... A61B 5/0422 |
| 9,472,019 | B2 | 10/2016 | Jenkins | |
| 2008/0194979 | A1 * | 8/2008 | Madry | ............... A61B 5/02405 600/523 |
| 2016/0166167 | A1 * | 6/2016 | Narayan | ................ A61B 5/042 600/510 |
| 2017/0281231 | A1 * | 10/2017 | Langell | .............. A61B 17/4241 |

OTHER PUBLICATIONS

Peters J, Ecabert O, Schramm H, Weese J. Discriminative boundary detection for model-based heart segmentation in CT images. InMedical Imaging 2007: Image Processing Mar. 3, 2007 (vol. 6512, p. 65120H). International Society for Optics and Photonics.*

Alliez P, Meyer M, Desbrun M. Interactive geometry remeshing. InACM Transactions on Graphics (TOG) Jul. 23, 2002 (vol. 21, No. 3, pp. 347-354). ACM.*

Bhakta D, Miller JM. Principles of electroanatomic mapping. Indian pacing and electrophysiology journal. Jan. 2008;8(1):32.*

European Search Report dated Jan. 31, 2018 from corresponding European Patent Application No. 17205480.1.

Frisch, Daniel, "Point2trimesh()—Distance Between Point and Triangulated Surface-Overview", Retrieved from the Internet: URL:http://de.mathworks.com, Sep. 25, 2016, pp. 1-5.

Frisch, Daniel, "Point2trimesh()—Distance Between Point and Triangulated Surface-Functions", Retrieved from the Internet: URL:http://de.mathworks.com, Sep. 25, 2016, pp. 1-10.

Hull, Doug, "Set-up: Finding Closest Point on a Surface", Retrieved from the Internet: URL:https://blogs.mathworks.com, May 5, 2010, p. 1.

* cited by examiner

UPDATING AN ELECTROANATOMICAL MAP

FIELD OF THE INVENTION

The present invention relates to computer models of three-dimensional surfaces, such as anatomical surfaces, and the visualization thereof.

BACKGROUND

Three-dimensional surfaces are often represented in computer memory by a contiguous collection of tiles, such as triangular tiles. Such a representation may be referred to as a "tesselation" or a "mesh."

A "local activation time" (LAT) of a particular area of the heart is the time at which the wavefront of electrical propagation passes through the area. A local activation time is typically measured from a particular reference time, such as a particular point in time in the QRS complex of a body-surface electrocardiogram (ECG) recording.

SUMMARY OF THE INVENTION

There is provided, in accordance with some embodiments of the present invention, a system for updating a mesh, which includes a plurality of vertices, representing an electroanatomical map of a surface of a heart. The system includes an electrical interface and a processor. The processor is configured to define a plurality of sample points on the mesh, such that a density of the sample points is greater than a density of the vertices, and to receive, via the electrical interface, a plurality of signals from an intrabody catheter, the signals indicating an electrical property of each of a plurality of locations on the surface of the heart. The processor is further configured to update the mesh in accordance with the electrical property, by, for each particular location of the locations, identifying a closest one of the sample points, which corresponds to a location that is closest to the particular location, relative to other ones of the sample points, subsequently, identifying, in a portion of the mesh in which the closest one of the sample points is located, a closest point, which corresponds to a location that is closest to the particular location, relative to other points in the portion of the mesh, and, subsequently, associating the closest point with the electrical property of the particular location.

In some embodiments, the processor is configured to define the sample points by uniformly sampling the mesh.

In some embodiments, the processor is configured to define the sample points by sampling the entire mesh.

In some embodiments, the processor is further configured to organize the sample points in a space-partitioning data structure, and the processor is configured to identify the closest one of the sample points by querying the space-partitioning data structure.

In some embodiments, the portion of the mesh consists of a tile in which the closest sample point is located, and a plurality of neighboring tiles that surround the tile in which the closest sample point is located.

In some embodiments, the neighboring tiles include each tile in the mesh that shares at least one vertex with the tile in which the closest sample point is located.

In some embodiments, the processor is configured to update the mesh by dividing a tile of the mesh that contains the closest point into a plurality of tiles that share a vertex located at the closest point.

In some embodiments, the processor is configured to update the mesh by recoloring the mesh in accordance with the electrical property.

In some embodiments, the processor is configured to update the mesh without changing a topology of the mesh.

In some embodiments, the processor is configured to identify the closest point by calculating a distance between the particular location and each plane corresponding to a respective tile in the portion of the mesh.

There is further provided, in accordance with some embodiments of the present invention, a method for updating a mesh, which includes a plurality of vertices, representing an electroanatomical map of a surface of a heart. The method includes, using a processor, defining a plurality of sample points on the mesh, such that a density of the sample points is greater than a density of the vertices, and receiving a plurality of signals from an intrabody catheter, the signals indicating an electrical property of each of a plurality of locations on the surface of the heart. The method further includes updating the mesh in accordance with the electrical property, by, for each particular location of the locations, identifying a closest one of the sample points, which corresponds to a location that is closest to the particular location, relative to other ones of the sample points, subsequently, identifying, in a portion of the mesh in which the closest one of the sample points is located, a closest point, which corresponds to a location that is closest to the particular location, relative to other points in the portion of the mesh, and, subsequently, associating the closest point with the electrical property of the particular location.

The present invention will be more fully understood from the following detailed description of embodiments thereof, taken together with the drawings, in which:

DETAILED DESCRIPTION OF EMBODIMENTS

Overview

Figure 1:
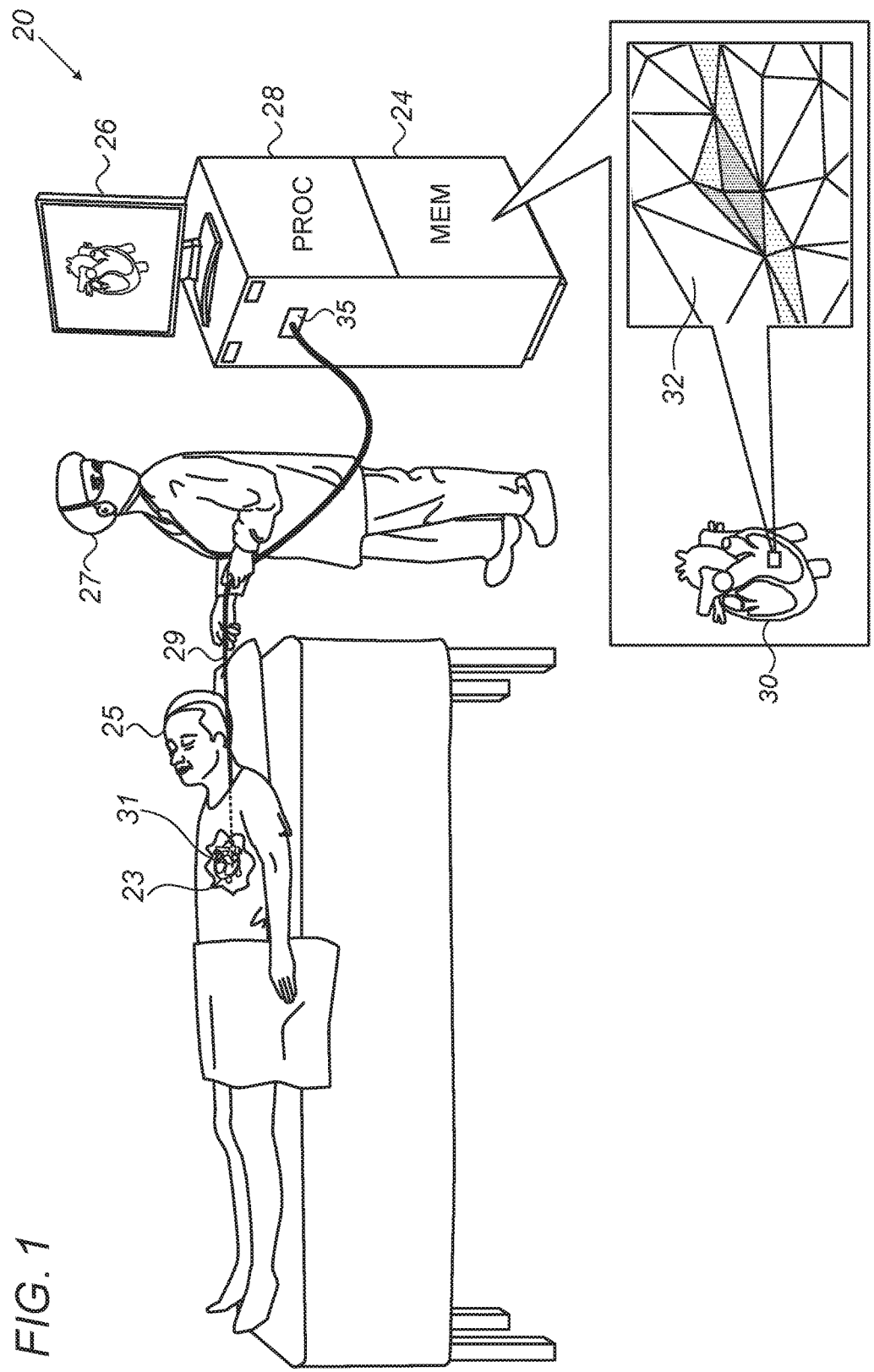
FIG. 1 is a schematic illustration of a system for updating a mesh that represents an electroanatomical map, in accordance with some embodiments of the present invention.

In some embodiments, an electroanatomical map of a surface of a subject's heart is constructed. As implied by the word "electroanatomical," such a map combines anatomical information relating to the structure of the heart with information relating to the electrical activity of the heart. Such a map is typically represented in a computer memory by a three-dimensional mesh that is colored, or otherwise annotated, in accordance with a measured electrical property of the surface. For example, the mesh may be colored in accordance with measured LATs or electrical potentials. Such a mesh is typically constructed from a plurality of points that correspond, respectively, to the locations at which the electrical property was measured, each of these points being associated with the value of the electrical property that was measured at the corresponding location. These points constitute the vertices of the tiles of the mesh, and are hence referred to hereinbelow as "vertices."

In some cases, it may be necessary to update an electroanatomical map with newly-acquired measurements. For example, following an ablation procedure, a physician may use a catheter to measure a plurality of LATs at various locations in the region of the ablated tissue. The mesh must then be recolored in this region, in order to accurately reflect the updated LAT values. In order to perform such an update, however, it is necessary to project each of the locations onto the mesh. In other words, for each given location at which an updated measurement was acquired, it is necessary to find the point on the mesh that corresponds to a location that is closest to the given location, such that this point may be associated with the updated measurement. (For simplicity, this point may referred to as the closest point to the given location.)

One hypothetical solution is to find, for each given location, the closest point on each of the mesh tiles, and to then project the given location onto the closest of these closest points. However, this technique, although accurate, is computationally intensive and slow. Another option is to project the location onto the closest vertex in the mesh. However, this technique, although fast, is not sufficiently accurate. Moreover, some tiles may be relatively large (i.e., some vertices may be relatively widely spaced), such that a projection onto a vertex does not necessarily constitute a helpful "initial" projection. In other words, even a subsequent, more accurate projection to the closest point in the vicinity of the closest vertex would not necessarily be sufficiently accurate, since the overall closest point on the mesh would not necessarily be contained in the vicinity of the closest vertex.

Embodiments of the present invention therefore provide a superior solution that is both fast and accurate. First, the mesh is sampled, typically uniformly, such as to yield a collection of sample points that is denser than the collection of vertices. Next, the closest sample point to the location is found, thus obtaining a rough, initial projection onto the mesh. This step is relatively fast, especially if a space-partitioning data structure, such as a k-d tree, is used to organize the sample points. Subsequently, a refined, more accurate projection is performed, by finding the closest point in the vicinity of the closest sample point. Since this more accurate projection does not operate on the entire mesh, but only on a limited portion thereof, the projection may be quickly performed.

System Description

Reference is initially made to FIG. 1, which is a schematic illustration of a system 20 for updating a mesh that represents an electroanatomical map, in accordance with some embodiments of the present invention. One commercial product embodying elements of system 20 is the CARTO® 3 System, available from Biosense Webster, Inc. This system may be modified by those skilled in the art to embody the principles of embodiments described herein.

FIG. 1 shows a physician 27 holding an intrabody catheter 29, a distal end 31 of which is disposed within the heart 23 of a subject 25. As physician 27 moves distal end 31 of catheter 29 along a surface (e.g., the inner or epicardial surface) of heart 23, one or more electrodes at the distal end of the catheter record intracardiac electrocardiographic (ECG) signals from a plurality of locations on the surface of the heart. A processor (PROC) 28 receives these ECG signals from the catheter via an electrical interface 35, which may comprise, for example, a port or other connector. The signals indicate one or more electrical properties, of the locations, that processor 28 identifies by analyzing the ECG signals. For example, processor may identify electrical potentials indicated by the ECG signals, and/or may compute LATs from the ECG signals.

During the procedure, and/or thereafter, processor 28 may retrieve a three-dimensional mesh 30, which represents an electroanatomical map of the subject's heart, from a computer memory (MEM) 24, and render mesh 30 on a display 26. Mesh 30 comprises a tesselation of tiles 32, which are typically triangular in shape. Mesh 30 is colored, and/or otherwise annotated, in accordance with an electrical property measured at the vertices of the tiles. (Interpolation may be used to color the areas of the mesh lying between the vertices.)

As described in detail below, as the processor identifies the heart's electrical properties from the ECG signals, the processor updates mesh 30, in accordance with the identified properties.

In general, processor 28 may be embodied as a single processor, or as a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2A:
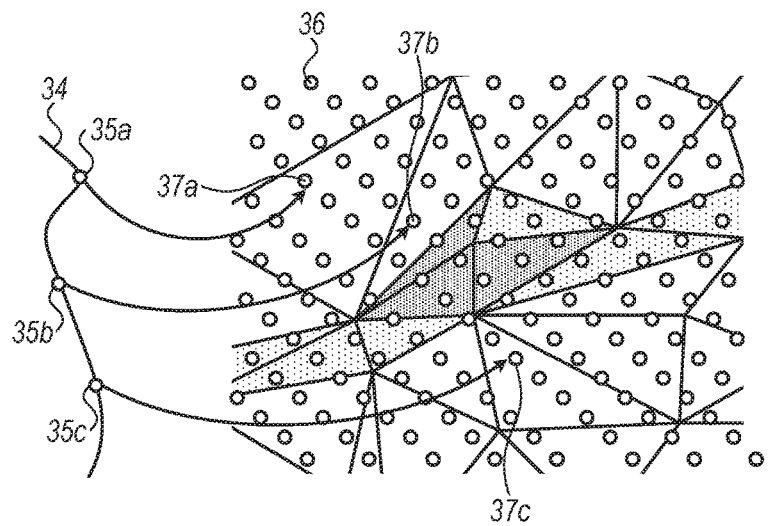
FIGS. 2A-C collectively show a method for updating a mesh, in accordance with some embodiments of the present invention.
Figure 2B:
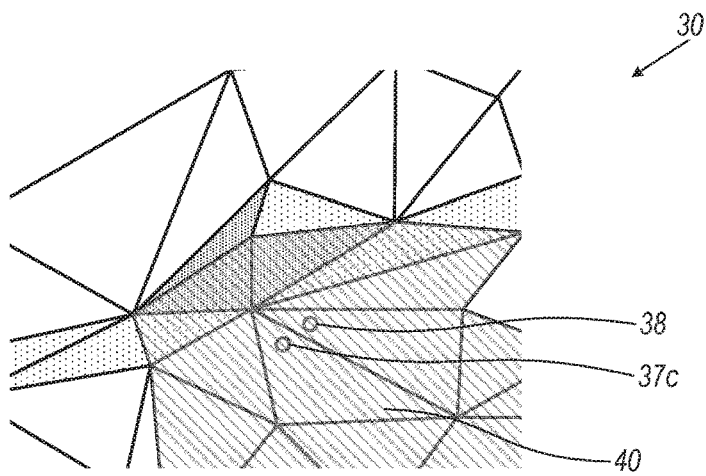
Figure 2C:
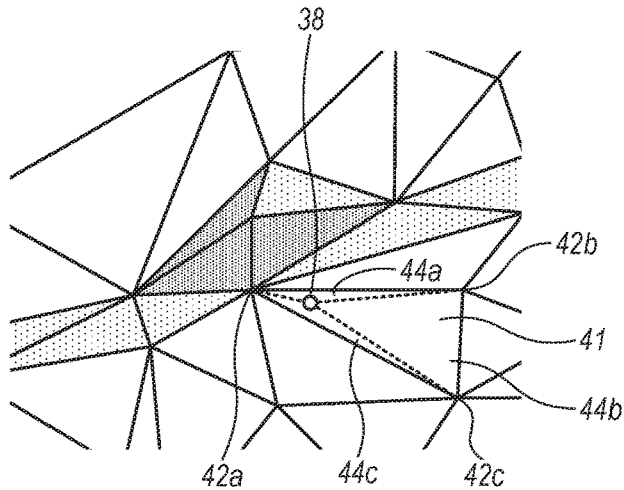

Reference is now made to FIGS. 2A-C, which collectively show a method, performed by processor 28, for updating mesh 30, in accordance with some embodiments of the present invention.

FIG. 2A depicts a scenario in which the catheter has acquired ECG signals at three locations 35a, 35b, and 35c on a surface 34 of a heart. As described above, processor 28 receives these signals, and then ascertains at least one property, such as an electrical property (e.g., an LAT), of each of these locations. Processor then updates mesh 30, in accordance with the property. First, the processor defines a plurality of sample points 36 on the mesh, typically by uniformly sampling the mesh. Next, for each particular location, the processor identifies the closest one of the sample points, which corresponds to a location that is closest to the particular location, relative to the other sample points. In other words, the processor projects each of the locations onto the closest one of the sample points. For example, FIG. 2A shows location 35a projected onto a sample point 37a, location 35b projected onto a sample point 37b, and location 35c projected onto a sample point 37c.

To illustrate the concept of a closest sample point, it will be assumed that location 35c has coordinates (3, 4, 5), and sample point 37c corresponds to a location with coordinates (3.1, 3.9, 4.95). (It is noted that, since the mesh only approximates the surface, each point on the mesh does not necessarily correspond to a location that is on the surface.) In this case, the distance between location 35c and sample point 37c is 0.15 ($\sqrt{(3.1-3)^2+(3.9-4)^2+(4.95-5)^2}=0.15$). (Since sample point 37c exists only as a virtual object that is stored in computer memory and displayed on-screen, this distance may be more precisely stated as the distance between location 35c and the "real-world" location that corresponds to sample point 37c. For simplicity, however, the present description refers to this distance as the distance between the location and the sample point.) Sample point 37c is thus closer to location 35c than, for example, another sample point corresponding to a location with coordinates (3.1, 3.8, 4.9). Sample point 37c is in fact closest to location 35c, assuming no other sample point has a distance to location 35c that is smaller than 0.15.

Since, typically, the processor receives ECG signals from a large number of locations spread over a large portion of surface 34, the processor typically samples the entire mesh, in order to facilitate projecting any given location onto any portion of the mesh. In some embodiments, however, if the locations are restricted to a particular portion of the surface, the processor may sample only a portion of the mesh that generally corresponds to the portion of the surface.

Typically, the processor organizes the sample points in a space-partitioning data structure, such as a k-dimensional (k-d) tree. The processor may then quickly identify the closest one of the sample points for each location, by querying the space-partitioning data structure.

FIG. 2B illustrates one way in which the initial, rough projection of FIG. 2A may be subsequently refined. In this refinement, the processor identifies a respective point on the mesh that is closest to each location. This refinement is illustrated for location 35c, whereby location 35c is projected onto a closest point 38, following its initial projection onto closest sample point 37c.

First, the processor identifies a portion of the mesh in which the closest sample point is located. Typically, this portion consists of the tile in which the closest sample point is located, and a plurality of neighboring tiles that surround the tile in which the closest sample point is located. For example, the neighboring tiles may include each tile in the mesh that shares at least one vertex with the tile in which the closest sample point is located. FIG. 2B illustrates such a case, by shading-in, with diagonal lines, the identified portion of the mesh in which closest sample point 37c is located. This portion includes a tile 40, which contains closest sample point 37c, along with each of the tiles that shares at least one vertex with tile 40.

Next, the processor identifies, in the identified portion of the mesh, the closest point 38 that corresponds to a location that is closest to location 35c, relative to other points in the identified portion of the mesh. In other words, the processor performs a more accurate projection of location 35c, onto the closest point in the identified portion of the mesh. Typically, to perform this projection, the processor calculates the distance between location 35c and each of the (planar) tiles in the identified portion of the mesh, using any suitable techniques known in the art for computing the distance between a point and a plane. (Since the tiles exist only as virtual objects that are stored in computer memory and displayed on-screen, it may be said, more precisely, that the processor calculates the distance between location 35c and each "real-world" plane that corresponds to a respective tile in the identified portion of the mesh. For simplicity, however, the present description refers to this distance as the distance between the location and the tile.) In calculating these distances, the processor considers every point in each tile, such that the processor finds the point that is, overall, closest to location 35c.

Thus, for example, assuming again that location 35c has coordinates (3, 4, 5), closest point 38 may correspond to a location with coordinates (3, 4, 5.05), such that the distance between location 35c and closest point 38 is only 0.05. Alternatively, for example, closest point 38 may correspond exactly to location 35c.

If the processor were to perform the more accurate projection of FIG. 2B without first performing the initial projection of FIG. 2A, the processor might need to consider every tile in the mesh for each location. Since, however, the initial projection of FIG. 2A reduces the "area of interest" to a smaller number of tiles, the more accurate projection of FIG. 2B may be performed relatively quickly. Moreover, as long as the sampling of the mesh is dense enough, the closest sample point will be relatively close to the overall closest point on the mesh, such that it is generally sufficient, when performing the more accurate projection, to consider a relatively small number of tiles in the vicinity of the closest sample point.

Subsequently, as shown in FIG. 2C, the processor updates the mesh, in accordance with the property that was measured at location 35c. Typically, in updating the mesh, the processor divides the tile 41 that contains closest point 38 into a plurality of tiles that share a vertex located at closest point 38, and further associates closest point 38 with the property.

For example, by way of illustration, it will be assumed that tile 41 has a first vertex 42a having coordinates (x0, y0, z0), a second vertex 42b having coordinates (x1, y1, z1), and a third vertex 42c having coordinates (x2, y2, z2), and that closest point 38 has coordinates (x3, y3, z3). It will be further assumed that first vertex 42a is associated with an LAT value of T0, second vertex 42b is associated with an LAT value of T1, and third vertex 42c is associated with an LAT value of T2, such that tile 41 may be defined by the following collection of data points: {(x0, y0, z0, T0), (x1, y1, z1, T1), (x2, y2, z2, T2)}.

The processor, upon identifying closest point 38, associates closest point 38 with an LAT value, measured at location 35c, of T3, and retiles the mesh to incorporate closest point 38, such that tile 41 is replaced by the following three new tiles:

(i) New tile 44a: {(x0, y0, z0, T0), (x1, y1, z1, T1), (x3, y3, z3, T3)}
(ii) New tile 44b: {(x1, y1, z1, T1), (x2, y2, z2, T2), (x3, y3, z3, T3)}
(iii) New tile 44c: {(x0, y0, z0, T0), (x2, y2, z2, T2), (x3, y3, z3, T3)}

In updating the mesh, the processor typically also recolors the mesh in accordance with the measured property. For example, referring again to the particular illustration shown in FIG. 2C, it is possible that T0=T1=T2, such that tile 41, prior to the updating of the mesh, was colored uniformly, in accordance with the value of these LATs. Assuming, however, that T3 is different from T0, T1, and T2, each of new tiles 44a-c would be colored non-uniformly, in accordance with the LAT gradient across the tile. The new coloring of the mesh would thus be different from the previous coloring of the mesh.

Typically, the processor also displays a marker over closest point 38, the marker indicating to the physician that data were acquired for closest point 38. (This marker may be identical to other markers displayed over other vertices of the mesh.) Subsequently, by clicking on the marker, the physician may view the data that were acquired.

It is noted that the updating of the mesh, as illustrated in FIGS. 2A-C, does not change the topology of the mesh, since the locations at which the measurements were acquired are projected onto the mesh. Even the retiling of the mesh, illustrated in FIG. 2C, does not change the topology of the mesh, since each of new tiles 44*a-c* is coplanar with original tile 41.

Figure 3:
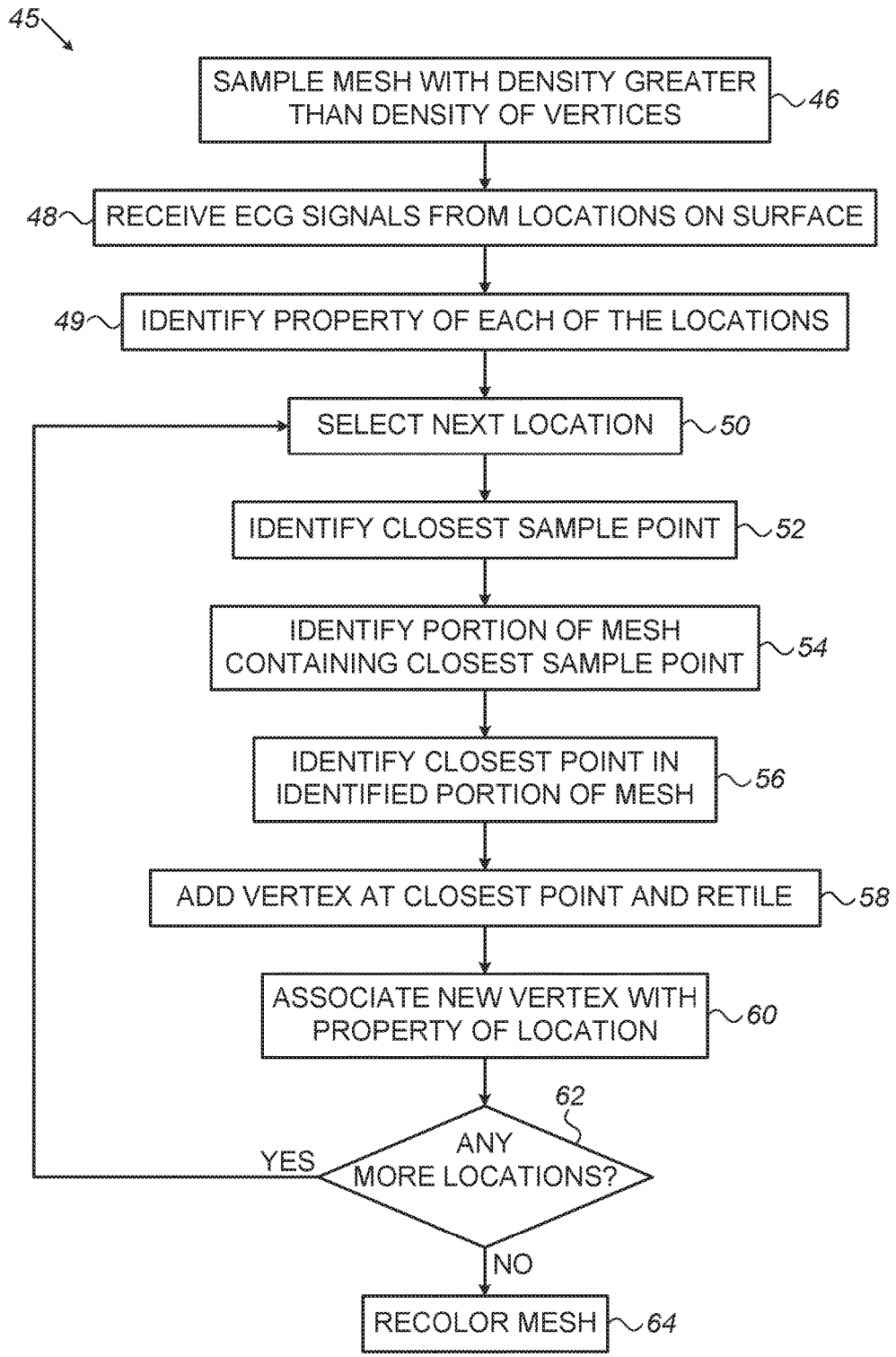
FIG. 3 is a flow diagram for a method for updating a mesh, in accordance with some embodiments of the present invention.

Reference is now made to FIG. 3, which is a flow diagram for a method 45 for updating mesh 30, in accordance with some embodiments of the present invention. Method 45 is performed by processor 28, generally as described above.

First, at a sampling step 46, the processor samples the mesh, such that the density of the sample points is greater than the density of the vertices. Next, the processor, at a receiving step 48, receives ECG signals from the intrabody catheter, acquired from various locations on the surface of the heart. (Receiving step 48 and property-identifying step 49 may be performed prior to sampling step 46.) By processing the signals, the processor identifies a property (such as an LAT) of each of the locations, at a property-identifying step 49. At a selecting step 50, the processor then selects one of the locations, and identifies the closest sample point to the selected location, at a closest-sample-point-identifying step 52. As described above, this constitutes a rough projection of the selected location onto the mesh.

Next, at a mesh-portion-identifying step 54, the processor identifies a portion of the mesh, such as a neighborhood of several tiles, that contains the closest sample point. Subsequently, at a closest-point-identifying step 56, the processor identifies the closest point on the mesh to the selected location; as described above, this constitutes a more accurate projection onto the mesh. Subsequently, at a retiling step 58, the processor adds a new vertex to the mesh at the closest point, and retiles the mesh accordingly, as shown in FIG. 2C. Next, or in conjunction with retiling step 58, the processor associates the new vertex with the identified property of the selected location, at an associating step 60.

Subsequently, at a checking step 62, the processor checks if any more locations await projection onto the mesh. If yes, the processor returns to selecting step 50, and then processes the next selected location at described above. Otherwise, the processor recolors the mesh, in accordance with the properties of the newly-added vertices.

In some embodiments, selecting step 50, closest-sample-point-identifying step 52, mesh-portion-identifying step 54, and closest-point-identifying step 56 are performed in real-time, during the acquisition of ECG signals from the surface of the heart. In other words, these steps may be performed in parallel with receiving step 48 and property-identifying step 49, such that the processor may project a first group of locations onto the mesh, while continuing to receive and process signals from a subsequent group of locations.

In some embodiments, the processor uses the projection techniques described herein to accurately place a marker, such as an icon, over the mesh, without necessarily updating the mesh itself. For example, given an electrode at a particular location on the surface of the heart, the processor may, as described herein, project the particular location onto the closest point on the mesh, and then display an icon representing the electrode over this closest point. Alternatively or additionally, using the projection techniques described herein, the processor may display an icon representing catheter 29 (FIG. 1) over the portion of the mesh that is closest to the catheter's location. Accurately placing such icons over the mesh may help guide the physician in acquiring ECG readings from the proper locations.

Although the present description relates mainly to electroanatomical maps, it is noted that the projection techniques described herein may be used for any suitable application in which a mesh model of a three-dimensional surface is updated in accordance with newly-acquired information about the surface, and/or in which markers are displayed over such a mesh to mark particular locations on the surface.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for updating a mesh representing an electroanatomical map of a surface of a heart, the mesh including a plurality of vertices, each vertex representing a first value of an electrical property at an anatomical location of the heart, the system comprising:
   an electrical interface; and
   a processor, configured:
      to define a plurality of sample points on the mesh, such that a density of the sample points is greater than a density of the vertices;
      to receive, via the electrical interface, a plurality of signals from an intrabody catheter, the signals indicating as second value of an electrical property of each of a plurality of locations on the surface of the heart; and
      to update the mesh in accordance with the second value of the electrical property, by, for each particular location of the locations:
         identifying a closest one of the sample points, which corresponds to a location that is closest to the particular location, relative to other ones of the sample points,
         subsequently, identifying, in a portion of the mesh in which the closest one of the sample points is located, a closest point, which corresponds to a location that is closest to the particular location, relative to other points in the portion of the mesh, and
         subsequently, associating the closest point with the electrical property of the particular location.

2. The system according to claim 1, wherein the processor is configured to define the sample points by uniformly sampling the mesh.

3. The system according to claim 1, wherein the processor is configured to define the sample points by sampling the entire mesh.

4. The system according to claim 1, wherein the processor is further configured to organize the sample points in a space-partitioning data structure, and wherein the processor is configured to identify the closest one of the sample points by querying the space-partitioning data structure.

5. The system according to claim 1, wherein the portion of the mesh consists of a tile in which the closest sample point is located, and a plurality of neighboring tiles that surround the tile in which the closest sample point is located.

6. The system according to claim 5, wherein the neighboring tiles include each tile in the mesh that shares at least one vertex with the tile in which the closest sample point is located.

7. The system according to claim 1, wherein the processor is configured to update the mesh by dividing a tile of the mesh that contains the closest point into a plurality of tiles that share a vertex located at the closest point.

8. The system according to claim 1, wherein the processor is configured to update the mesh by recoloring the mesh in accordance with the electrical property.

9. The system according to claim 1, wherein the processor is configured to update the mesh without changing a topology of the mesh.

10. The system according to claim 1, wherein the processor is configured to identify the closest point by calculating a distance between the particular location and each plane corresponding to a respective tile in the portion of the mesh.

11. A method for updating a mesh representing an electroanatomical map of a surface of a heart, the mesh including a plurality of vertices, each vertex representing a first value of an electrical property at an anatomical location of the heart, the method comprising:

using a processor, defining a plurality of sample points on the mesh, such that a density of the sample points is greater than a density of the vertices;

receiving a plurality of signals from an intrabody catheter, the signals indicating a second value of an electrical property of each of a plurality of locations on the surface of the heart; and updating the mesh in accordance with the second value of the electrical property, by, for each particular location of the locations:

identifying a closest one of the sample points, which corresponds to a location that is closest to the particular location, relative to other ones of the sample points, subsequently, identifying, in a portion of the mesh in which the closest one of the sample points is located, a closest point, which corresponds to a location that is closest to the particular location, relative to other points in the portion of the mesh, and subsequently, associating the closest point with the electrical property of the particular location.

12. The method according to claim 11, wherein defining the sample points comprises defining the sample points by uniformly sampling the mesh.

13. The method according to claim 11, wherein defining the sample points comprises defining the sample points by sampling the entire mesh.

14. The method according to claim 11, further comprising organizing the sample points in a space-partitioning data structure, wherein identifying the closest one of the sample points comprises identifying the closest one of the sample points by querying the space-partitioning data structure.

15. The method according to claim 11, wherein the portion of the mesh consists of a tile in which the closest sample point is located, and a plurality of neighboring tiles that surround the tile in which the closest sample point is located.

16. The method according to claim 15, wherein the neighboring tiles include each tile in the mesh that shares at least one vertex with the tile in which the closest sample point is located.

17. The method according to claim 11, wherein updating the mesh comprises dividing a tile of the mesh that contains the closest point into a plurality of tiles that share a vertex located at the closest point.

18. The method according to claim 11, wherein updating the mesh comprises updating the mesh by recoloring the mesh in accordance with the electrical property.

19. The method according to claim 11, wherein updating the mesh comprises updating the mesh without changing a topology of the mesh.

20. The method according to claim 11, wherein the processor is configured to identify the closest point by calculating a distance between the particular location and each plane corresponding to a respective tile in the portion of the mesh.

* * * * *